US012569596B2

(12) United States Patent (10) Patent No.: US 12,569,596 B2
Heinsch et al. (45) Date of Patent: Mar. 10, 2026

(54) VASCULAR PROSTHESIS

(71) Applicant: E.S. BIO-TECH LIMITED, Limassol (CY)

(72) Inventors: Manfred Heinsch, Schöneck (DE); Mirko Doss, Frankfurt am Main (DE); Martin Brüning, Ebersbach (DE); Erhard Müller, Stuttgart (DE); Michael Ullmann, Leonberg (DE)

(73) Assignee: E.S. BIO-TECH LIMITED, Limassol (CY)

( * ) Notice: Subject to any disclaimer, the term of this patent is extended or adjusted under 35 U.S.C. 154(b) by 1265 days.

(21) Appl. No.: 17/004,328

(22) Filed: Aug. 27, 2020

(65) Prior Publication Data

US 2021/0085830 A1 Mar. 25, 2021

(30) Foreign Application Priority Data

Sep. 20, 2019 (DE) .......................... 102019125367.5

(51) Int. Cl.
A61L 27/50 (2006.01)
A61F 2/06 (2013.01)
(Continued)

(52) U.S. Cl.
CPC .............. A61L 27/507 (2013.01); A61F 2/06 (2013.01); D02G 3/045 (2013.01); D02G 3/32 (2013.01);
(Continued)

(58) Field of Classification Search
CPC ....... A61L 27/507; A61L 27/18; D02G 3/045; D02G 3/32; D02G 3/38; D02G 3/448; A61F 2/064
See application file for complete search history.

(56) References Cited

U.S. PATENT DOCUMENTS 4,990,158 A * 2/1991 Kaplan .................. D02G 3/328
623/1.46
5,147,400 A * 9/1992 Kaplan .................. D02G 3/448
623/1.53
(Continued)

FOREIGN PATENT DOCUMENTS

DE 102006028221 A1 12/2007
DE 102009052349 A1 8/2011
(Continued)

OTHER PUBLICATIONS

TW I512156 B1—Translation (Year: 2015).*

*Primary Examiner* — Sarah W Aleman
*Assistant Examiner* — Rebecca Lynee Zimmerman
(74) *Attorney, Agent, or Firm* — Richard M. Goldberg

(57) ABSTRACT

A vascular prosthesis (1) for connection to a natural cardio-vascular system, includes a volume chamber (2), wherein the volume chamber (2) has, in a blood pressure range below a pressure threshold value D, a pressure-expansion behavior substantially corresponding to the pressure-expansion behavior of a natural blood vessel, while the volume of the volume chamber (2), depending on the pressure, increases by at least 10 cm$^3$ in a blood pressure range above the pressure threshold value D. The vascular prosthesis (1) is configured as a textile tube, wherein the textile tube includes in the region of the volume chamber (2) an elastic yarn having a core made from silicone yarn around which a yarn made from polyethylene terephthalate (PET) is wrapped.

16 Claims, 4 Drawing Sheets

(51) Int. Cl.

| | | |
|---|---|---|
| *D02G 3/04* | (2006.01) | |
| *D02G 3/32* | (2006.01) | |
| *D02G 3/38* | (2006.01) | |
| *D02G 3/44* | (2006.01) | |

(52) U.S. Cl.

CPC .............. *D02G 3/38* (2013.01); *D02G 3/448* (2013.01); *A61F 2002/068* (2013.01)

(56) References Cited

U.S. PATENT DOCUMENTS

| | | | | |
|---|---|---|---|---|
| 5,989,287 | A | * | 11/1999 | Yang ...................... A61B 17/11 |
| | | | | 623/1.36 |
| 2001/0000188 | A1 | * | 4/2001 | Lenker ...................... A61F 2/07 |
| | | | | 623/1.13 |
| 2017/0027682 | A1 | * | 2/2017 | Merk ........................ A61F 2/07 |
| 2018/0202082 | A1 | * | 7/2018 | Van Hulle ................. A61F 2/07 |
| 2019/0015192 | A1 | * | 1/2019 | Nakazawa ............... D06C 7/02 |

FOREIGN PATENT DOCUMENTS

| | | | | |
|---|---|---|---|---|
| EP | 2319454 | A1 | | 5/2011 |
| EP | 2574305 | B1 | | 4/2013 |
| JP | S49-28898 | U | | 3/1974 |
| JP | H8-500759 | A | | 1/1996 |
| JP | 2018-523503 | A | | 8/2018 |
| TW | 512156 | B1 | * | 12/2015 |
| WO | 94-24960 | A | | 11/1994 |

* cited by examiner

9

11

10

9

12

10

9

13

10

VASCULAR PROSTHESIS

BACKGROUND OF THE INVENTION

The invention relates to a vascular prosthesis for connection to a natural cardiovascular system, comprising a volume chamber, wherein the volume chamber has, in a blood pressure range below a pressure threshold value D, a pressure-expansion behavior substantially corresponding to the pressure-expansion behavior of a natural blood vessel, while the volume of the volume chamber, depending on the pressure, increases by at least 10 cm$^3$ in a blood pressure range above the pressure threshold value. The invention also relates to a method for producing such a vascular prosthesis.

The replacement of diseased portions of the aorta with plastic vascular prostheses in the form of a bridging graft or the circumvention of diseased portions of the aorta in the form of a bypass are long-established surgical methods. The prostheses used in the process are usually manufactured as textile tube prostheses from synthetic polymers that are non-resorbable by the body, such as polytetrafluoroethylene (PTFE), or polyesters, such as polyethylene terephthalate (PET), by weaving or knitting. If necessary, such vascular prosthesis may also be configured in a branched manner, as so-called Y-prostheses.

Though the vascular prostheses employed today are longitudinally and transversely expansible to a small extent due to measures such as pleating or crimping, they do not have the elastic properties of the tissue of a natural aorta or of natural arteries. In particular, they are not sufficiently capable of emulating the Windkessel function of the natural vessels. The Windkessel function is understood to be the short-term retention in the elastic arteries of a part of the blood volume ejected by the heart during the systole and its continuous discharge during the diastole, whereby the blood flow is homogenized on the whole and the pressure difference between the systole and the diastole is reduced. In this case, the short-term storage and subsequent discharge of the blood volume is mainly caused by the elastic properties of the natural vascular walls which, having been expanded slightly during the systole, tend to return to their initial state during the diastole. So far, known vascular prostheses can emulate this property only to an insufficient extent.

The lack of elasticity of the vascular prostheses, given long-term application in the human body as intended, has a negative effect on the heart, the aorta and the vascular prosthesis itself. The replacement of the diseased aorta segment by interposition of a non-elastic vascular prosthesis is followed by a disparity between the volume capacity properties of the remaining natural aorta and the implanted more rigid vascular prosthesis. This disparity is also referred to as compliance disparity. In this case, the lack of elasticity of a vascular prosthesis implanted in the region of the aorta ascendens close to the heart affects the function of the aortic valve if the latter was preserved during the aortic replacement, so that the aortic valve may become leaky. In addition, the blood pressure is altered in an adverse manner with regard to the amplitude level and shape by the lack of elasticity. The loss or impairment of the Windkessel function of the aorta results, as a whole, in adverse hemodynamic changes including an increase in pulse wave velocity and a steeper rise of the blood pressure curve with a blood pressure amplitude that is increased on the whole.

These adverse blood pressure changes, which result from the compliance disparity, constitute a permanent stress on the heart that may lead to muscular hypertrophy (thickening of the cardiac walls) and an increasing dysfunction in the form of cardiac insufficiency (weakness of the heart). In addition, the increased stress resulting from the blood pressure changes has a negative effect on the remaining natural aorta and its connection points with the implanted vascular prosthesis. Here, a so-called anastomotic aneurysm may be formed, i.e. a dilation or sacculation in the connecting region of the prosthesis and the aorta, which may possibly have to be repaired surgically. In addition, the nonphysiological blood pressure stress arising immediately subsequent to the implantation of the prosthesis may result in an occasionally considerable and non-reversible increase of the diameter of the prosthesis, which requires subsequent observation and regular monitoring. This is usually done by annual CT examinations, which are in turn accompanied by an increased radiation exposure. If there are indications that the vascular prosthesis or the connection point are in danger of tearing, the vascular prosthesis has to be surgically replaced, which entails a significantly increased operative risk.

Vascular prostheses are already known which, due to their particular design, are at least partially capable of emulating the natural Windkessel function. For example, EP 2 574 305 B1 describes a compensating vessel for influencing blood pressure, comprising a volume chamber and connecting means for connecting the volume chamber to a natural cardiovascular system, wherein a volume change of the volume chamber can be caused by a pressure change in the cardiovascular system, and adaptation means, which limit the volume change of the volume chamber in a lower pressure range below a pressure threshold value of at least 100 mmHg to a maximum of 10 cm$^3$, and which cause a volume change of the volume chamber of at least 10 cm$^3$ in an upper pressure range between the pressure threshold value and 150 mmHg. In this case, the adaptation means comprise a frame and at least one resilient body cooperating therewith, wherein the frame and the resilient body are disposed outside the volume chamber and the frame comprises two end parts and at least three support bars, which connect the two end parts and between which the at least one resilient body extends. The structure of the compensating vessel is comparatively complex and complicated. In addition, the compensating vessel according to EP 2 574 305 B1 cannot be implanted by minimally invasive surgery. Improvements appear to be necessary in both cases. Moreover, an improvement with regard to the integration behavior of the vascular prosthesis is intended.

SUMMARY OF THE INVENTION

It is the object of the present invention to provide a vascular prosthesis whose properties match the properties of natural blood vessels to a greater extent than is the case in vascular prostheses known from the prior art, and which has a simple structure and can be implanted by minimally invasive surgery at the same time. It is another object of the invention to specify a method for producing such a vascular prosthesis.

These objects are achieved by a vascular prosthesis having the features of the independent patent claim 1 and a method for producing a vascular prosthesis having the features of the independent patent claim.

Advantageous embodiments and developments of the invention are the subject matter of the dependent claims.

According to the patent claims, the invention is a vascular prosthesis for connection to a natural cardiovascular system, comprising a volume chamber, wherein the volume chamber has, in a blood pressure range below a pressure threshold value D, a pressure-expansion behavior substantially corresponding to the pressure-expansion behavior of a natural blood vessel, while the volume of the volume chamber, depending on the pressure, increases by at least 10 cm³ in a blood pressure range above the pressure threshold value D. The vascular prosthesis according to the invention is characterized in that it is configured as a textile tube, wherein the textile tube includes in the region of the volume chamber an elastic yarn having a core made from silicone yarn around which a yarn made from polyethylene terephthalate (PET) is wrapped.

In other words, the invention is a textile, tube-shaped vascular prosthesis, whose volume increases by radial expansion in the elastic region from a defined pressure threshold value D, and which thus provides a defined additional volume, wherein the volume change or the radial expansion is largely reversible and the original, non-pressurized volume is largely restored again after a drop below the pressure threshold value D. In this case, the vascular prosthesis according to the invention is primarily characterized by the special material from which the volume chamber is fabricated completely or in part. This material includes a special elastic yarn formed from a core of silicone yarn, around which a wrapping yarn of polyethylene terephthalate (PET) is wrapped. In this case, the material silicone has excellent elastic properties and contributes to the volume of the volume chamber increasing under increasing pressure and decreasing again to the same extent under decreasing pressure. Thus, the novel vascular prosthesis has a compliance identical to that of the aorta in the range of physiological blood pressures. The simultaneous use of PET for wrapping the silicone yarn contributes to the volume of the volume chamber increasing significantly only in the case of blood pressures above a pre-settable pressure threshold value D and to this growth in volume being limited as a whole, so that a predetermined maximum increase in volume is not exceeded even for very high blood pressures. Due to the high elasticity and the accompanying restoring forces during the expansion of the elastic yarn used, all expansions of the volume chamber are reversible, whereby the properties of natural blood vessels can be emulated superbly.

According to the patent claims, the volume chamber has, in a blood pressure range below a pressure threshold value D, a pressure-expansion behavior substantially corresponding to the pressure-expansion behavior of a natural blood vessel. This is to be understood to mean that, below the pressure threshold value D, the volume of the volume chamber does not change beyond the minimum expansions required for maintaining the Windkessel function. In particular, these expansions are reversible due to the elasticity of the material.

Subsequent to the implantation of the vascular prosthesis according to the invention, the volume chamber of the vascular prosthesis, due to the diastolic blood pressure (lower blood pressure value) prevalent in the aorta, first expands up to the existing aortic diameter. Within the context of the normal action of the heart including the ejection of a certain blood volume (stroke volume), the blood pressure in the aorta or the vascular prosthesis rises until reaching the systolic pressure (upper blood pressure value). Therefore, the vascular prosthesis expands in the region of the elastic volume chamber and converts a part of the kinetic ejection energy into potential energy of elastic deformation. When the heart relaxes during the diastole and the blood pressure drops accordingly, the vascular prosthesis, which is configured to be elastic in the region of the volume chamber, releases the stored energy again due to the action of the restoring force and ejects the stored blood volume in the process. This corresponds to the normal Windkessel function of the aorta. Thus, the adverse changes of the blood pressure conditions including an acceleration of the pulse wave velocity and a rise in the blood pressure curve and amplitude as well as the negative long-term consequences connected therewith, which occur after an implantation of rigid vascular prostheses, do not occur after the implantation of the elastic vascular prosthesis according to the invention.

However, the vascular prosthesis according to the invention is not only capable of emulating the natural Windkessel function very well. In the case of an existing elevated blood pressure, it also has a pronounced blood pressure-lowering effect, which can also be ascribed to the elastic configuration of the volume chamber of the vascular prosthesis. Due to the specific volume capacity properties, according to the invention, a lowering effect occurs only in the case of an elevated blood pressure, whereas a normal or low blood pressure is not lowered further. According to the invention, it is provided that, below the pressure threshold value D, the volume of the volume chamber remains substantially unchanged and does not change beyond the minimum expansions required for maintaining the Windkessel function. A substantial and largely reversible radial expansion occurs only upon the pressure threshold value D being exceeded. In this case, the pressure threshold value D may be, for example, 100 mmHg or at least 120 mmHg. The pressure-dependent increase in volume of the volume chamber upon the pressure threshold value D being exceeded may be 10-80 cm³, preferably 40-60 cm³. In each case, an upper pre-settable limit of the increase in volume is not exceeded. This limitation of the growth in volume is substantially caused by wrapping the silicone yarn with PET. In this context, and in the pre-setting of the pressure threshold value D and of the possible growth in volume, parameters defining the specific textile tube, such as the thread count, filament number, weave construction etc. play an additional role, which will be explained in more detail below.

Because of these properties, the application of the elastic vascular prosthesis according to the invention in patients with therapy-resistant arterial hypertension, i.e. high blood pressure that does not respond to drug therapy, is conceivable as an interventional long-term alternative for drug therapy. For example, beside its use as an aortic replacement, the elastic vascular prosthesis according to the invention could additionally be implanted, in the course of a necessary heart operation in patients with a therapy-resistant hypertension, in the form of an aortic bypass as a permanently blood pressure-lowering measure. In this case, it is conceivable in principle to carry out the implantation in a minimally invasive manner and thus, given a corresponding indication, also as a primary intervention for permanently lowering blood pressure.

Thus, the vascular prosthesis according to the invention has highly adaptive properties in that it emulates the natural Windkessel function of the natural vessels very well at normal blood pressures and thus constitutes an excellent substitute for a portion of a natural blood vessel whereas, in the event of high blood pressures, it also has a pronounced blood pressure-lowering effect due to an additional and significant growth in volume that sets in only in that case. Because of the material used, the significant volume changes at high blood pressures are in this case largely reversible, so that the original, non-pressurized volume of the volume change is largely restored again after a drop below the pressure threshold value D. Therefore, the vascular prosthesis according to the invention not only exhibits good expansibility but also a high level of elasticity at the same time.

Finally, it is also conceivable to use the elastic vascular prosthesis according to the invention as an aortocoronary bypass. A surgically applied aortocoronary bypass bridges existing narrow portions of the coronary vessels, so-called coronary stenoses, and conducts the blood from the aorta to behind the coronary stenosis and towards the cardiac muscle, whereby the blood supply to the cardiac muscle is ensured. The body's own veins from the leg or, due to their elastic properties, preferably the body's own arteries, e.g. the thoracic artery, were usually used so far. Experiments with previously known artificial vascular prostheses as an aortocoronary bypass material were unsuccessful due to the lack of elasticity and the high rate of occlusion of the small-lumen vascular prostheses. This restriction could be eliminated with the elastic vascular prosthesis according to the invention, so that the harvesting of autologous veins from the leg or arteries from the inner thoracic wall during an aortocoronary bypass operation would no longer be required. Thus, both the surgical trauma and the accompanying surgical risks (post-operative bleeding, impaired wound healing and infections at the site of the operation) could be minimized and the surgery time could be significantly reduced. In addition to immediate health benefits for the patient, this would also have positive health-economic effects.

In principle, the special properties, i.e. the pressure-dependent increase in volume of the volume chamber when a pressure threshold value D is exceeded and the return of the volume chamber into the initial state when the pressure drops below the pressure threshold value D, as well as the pressure-expansion behavior, which is exhibited at blood pressures below the pressure threshold value D and which largely corresponds to that of a natural vessel, are substantially caused by the material combination of silicone and PET in a special elastic yarn suitable for medical use. In this case, the specific volume pressure curve for a given vascular prosthesis can be adjusted by numerous parameters. This includes variations of the constitution and configuration of the elastic yarn, in particular of the starting materials silicone yarn and PET wrapping yarn, and of the PET yarns used additionally for manufacturing the textile tube, but also variations in the configuration of the textile tube manufactured, in particular woven, using the elastic yarn.

According to one embodiment of the invention, the silicone yarn forming the core of the elastic yarn may be formed from silicone with a Shore hardness of 30 to 70, preferably of 40 to 60.

The elastic yarn formed of silicone yarn and PET wrapping yarn may have a thread count of 100 to 3000 dtex, preferably of 200 to 2000 dtex.

The PET wrapping yarn may have a thread count of 30 to 150 dtex, preferably of 50 to 110 dtex. In this case, the PET wrapping yarn may be wrapped around the silicone yarn once or multiple times, wherein several layers of PET wrapping yarn come to lie on the silicone yarn in the case of a multiple wrap. Accordingly, in a double wrap, the PET wrapping yarn rests on the silicone yarn in two layers. The pressure-expansion behavior of the elastic yarn can be influenced by the selection of the fineness of the PET wrapping yarn, as well as by means of the number and density of the wraps and the pitch at which the PET wrapping yarn is wrapped around the silicone yarn.

One embodiment of the invention provides that the vascular prosthesis is configured as a fabric tube, in particular as a seamless fabric tube, consisting of warp threads and weft threads, wherein the weft threads in the region of the volume chamber are formed from the elastic yarn. The warp threads may be formed from a PET yarn, for example. The PET yarn forming the warp threads may have a thread count of 50 to 300 dtex and be configured as a multifilament yarn consisting of 20 to 300 filaments, for example. In this case, for the purposes of the invention, a flat yarn or a textured yarn may be used as the PET yarn for the warp threads; a flat yarn or high shrinkage yarn may be used for the warp threads in regions adjacent to the volume chamber, e.g. in the region of the connecting portions explained in yet more detail below. Also, different PET yarns may be used for different portions of the vascular prosthesis; for example, a PET flat yarn may be used for the ground warp, and a PET textured yarn for the pile warp.

One property of high shrinkage yarn is that it contracts under the influx of heat. This property may be exploited, because if high shrinkage yarn is used, the woven fabric or knitted fabric or knit forming the textile tube can be caused to become denser by a final thermosetting process.

As an alternative, it is also conceivable that, if the vascular prosthesis is configured as a fabric tube, both the warp threads and the weft threads in the region of the volume chamber are formed from the elastic yarn.

Different weaving constructions may form the basis for forming the fabric tube. For example, the fabric tube may be woven with a twill weave or a satin weave or a plain weave or with a modification of one of these weaving constructions. In principle, the fabric tube may be formed with a single weaving construction; however, the fabric tube may also include portions that are formed with different weaving constructions. Among other things, the force-expansion behavior of the fabric tube can be influenced by the choice of weaving construction.

The force-expansion behavior of the fabric tube can also be influenced by the choice of yarn density, i.e. the number of threads per cm, both in the warp direction and in the weft direction.

The vascular prosthesis has connecting portions at its two ends, for suturing the vascular prosthesis to the ends of a natural blood vessel. With respect to the material and elasticity, these connecting portions may be configured the same as the volume chamber or differently from the volume chamber.

For example, it may be provided that the vascular prosthesis comprises connecting portions adjacent to the volume chamber, for connection to the natural cardiovascular system, wherein the connecting portions have a lower elasticity than the volume chamber. In other words, in this embodiment of the invention it is provided that the vascular prosthesis has portions with different elasticities, wherein a central portion forming the volume chamber has a higher elasticity than the connecting portions adjacent to both sides of the volume chamber. In particular, the connecting portions may be configured in a non-elastic manner. For example, they may be formed as a woven fabric, in which both the warp and weft threads are formed from a multifilament yarn of PET. In contrast to the region of the volume chamber, no elastic yarn is used in the adjacent connecting portions in this variant.

Alternatively, it is also possible that end-side portions of the volume chamber function as connecting portions. In this case, the vascular prosthesis as a whole can be formed from a uniform material and have a substantially uniform elasticity.

According to one embodiment, the vascular prosthesis according to the invention can have a multi-layer, in particular double-layer, configuration in the region of the connecting portions. This increases suture tear strength, i.e. the probability of the suture, which connects the vascular prosthesis with the natural vascular system, being ripped out can be reduced considerably. A multi-layer configuration may be obtained, for example, by turning or folding back and, if necessary, sewing together the textile tube in the region of the connecting portions.

According to one embodiment of the invention, the vascular prosthesis may have a dumbbell-shaped configuration such that, in a non-pressurized state, it is conically expanded in the region of the connecting portions compared with the central region of the volume chamber. In other words, in a non-pressurized state, the vascular prosthesis in this embodiment has a smaller diameter in the region of the volume chamber than in the region of the connecting portions, whose diameter conically expands starting from the diameter of the volume chamber towards the ends of the vascular prosthesis. In this case, the diameter of the vascular prosthesis in the region of the connecting portions may be larger by about one third than the diameter of the volume chamber in a non-pressurized state. It was found that the natural compliance of the aorta can be emulated particularly well by means of such a dumbbell-shaped configuration of the vascular prosthesis.

The vascular prosthesis may have a total length of about 15 cm to 25 cm, wherein the volume chamber has a length of about 10 cm to 15 cm and the connecting portions which, if necessary, are adjacent to both sides of the volume chamber, may each have a length of about 3 cm to 8 cm. By folding it back in the region of the connecting portions as described above, the length of the connecting portions can in this case varied and adapted to the conditions to a certain extent. The diameter of the vascular prosthesis in the non-pressurized state may be 15 mm to 20 mm in the central region of the volume chamber. In one embodiment of the vascular prosthesis with conically expanded connecting portions, the diameter may expand to about 25 mm to 33 mm.

In order to ensure the initial seal, the vascular prosthesis may be impregnated with crosslinked gelatin or coated with a synthetic polymer, e.g. silicone.

Finally, the invention according to the method patent claim also relates to a method for producing a vascular prosthesis according to the invention. Here, the method includes the following steps:

providing weft and warp threads, wherein the weft threads are formed from the elastic yarn at least in the region of the volume chamber,
  warping the ground and pile warps,
  weaving the textile tube on a shuttle ribbon loom,
  thermosetting the woven textile tube,
  washing the vascular prosthesis in order to remove finishing agents.

In summary, the vascular prosthesis according to the invention, compared to known vascular prostheses, has the advantage of a very simple structure because it obtains the required properties mainly from the material from which it is made. A structure of the vascular prosthesis that is complex and defect-prone, e.g. with adaptation means consisting of a frame and a clamped-in spring body that externally surround the volume chamber, can thus be omitted.

The elasticity and volume capacity (compliance) of the elastic textile vascular prosthesis according to the invention correspond to those of the natural aorta. Thus, the compliance disparity between the vascular prosthesis and the aorta, which exists in rigid vascular prostheses, is eliminated, which has a favorable effect on the heart, aorta and the vascular prosthesis itself in the designated long-term application. Thus, the above-described negative consequences on the heart, aorta and vascular prosthesis subsequent to the implantation of the vascular prosthesis can be avoided.

The vascular prosthesis according to the invention is particularly suitable for replacing and bridging diseased portions of the aorta, but also larger, medium and smaller arteries, and as a vascular prosthesis for aortocoronary bypasses.

BRIEF DESCRIPTION OF THE DRAWINGS

The invention will be explained in more detail below with reference to exemplary embodiments and to the attached schematic drawings. In the Figures.

DETAILED DESCRIPTION

Figures 1, 2, 3:
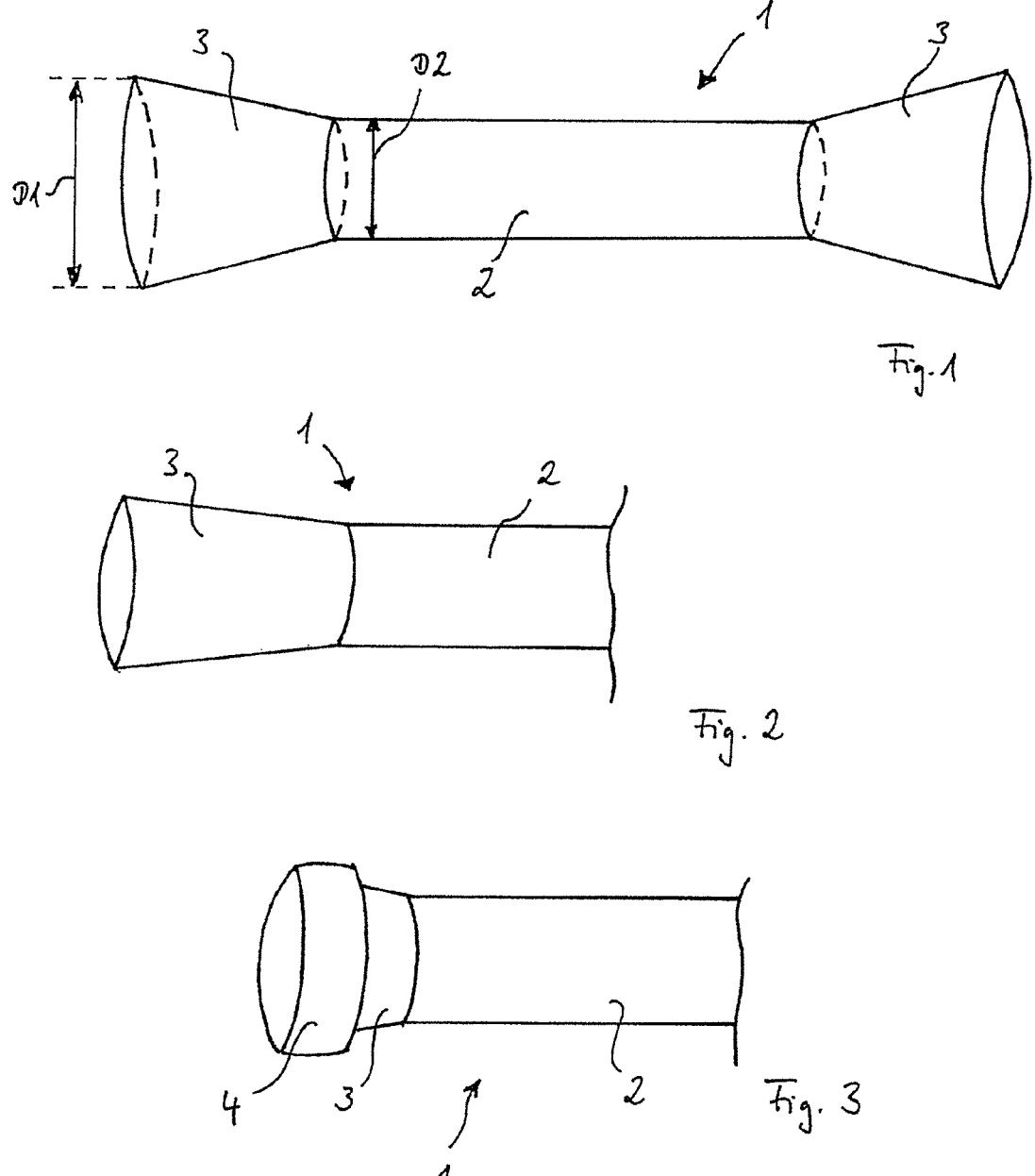
FIG. 1: shows a first embodiment of the elastic vascular prosthesis in a schematic perspective view.
FIG. 2: shows a portion from an illustration of a second embodiment of the elastic vascular prosthesis.
FIG. 3: shows a portion from an illustration of a third embodiment of the elastic vascular prosthesis.
Figure 6:
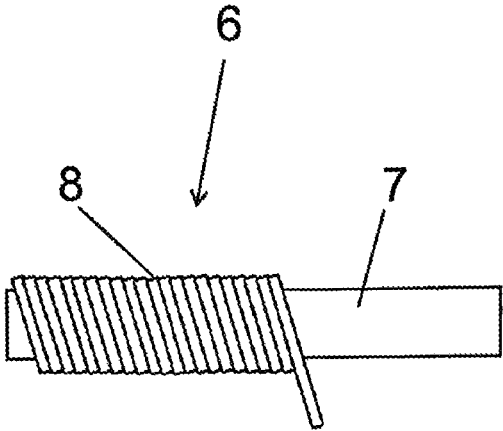
FIG. 6: shows the vascular prosthesis being configured as a textile tube including a core made from silicone yarn around which a yarn made from polyethylene terephthalate (PET) is wrapped.
Figures 7, 8, 9:
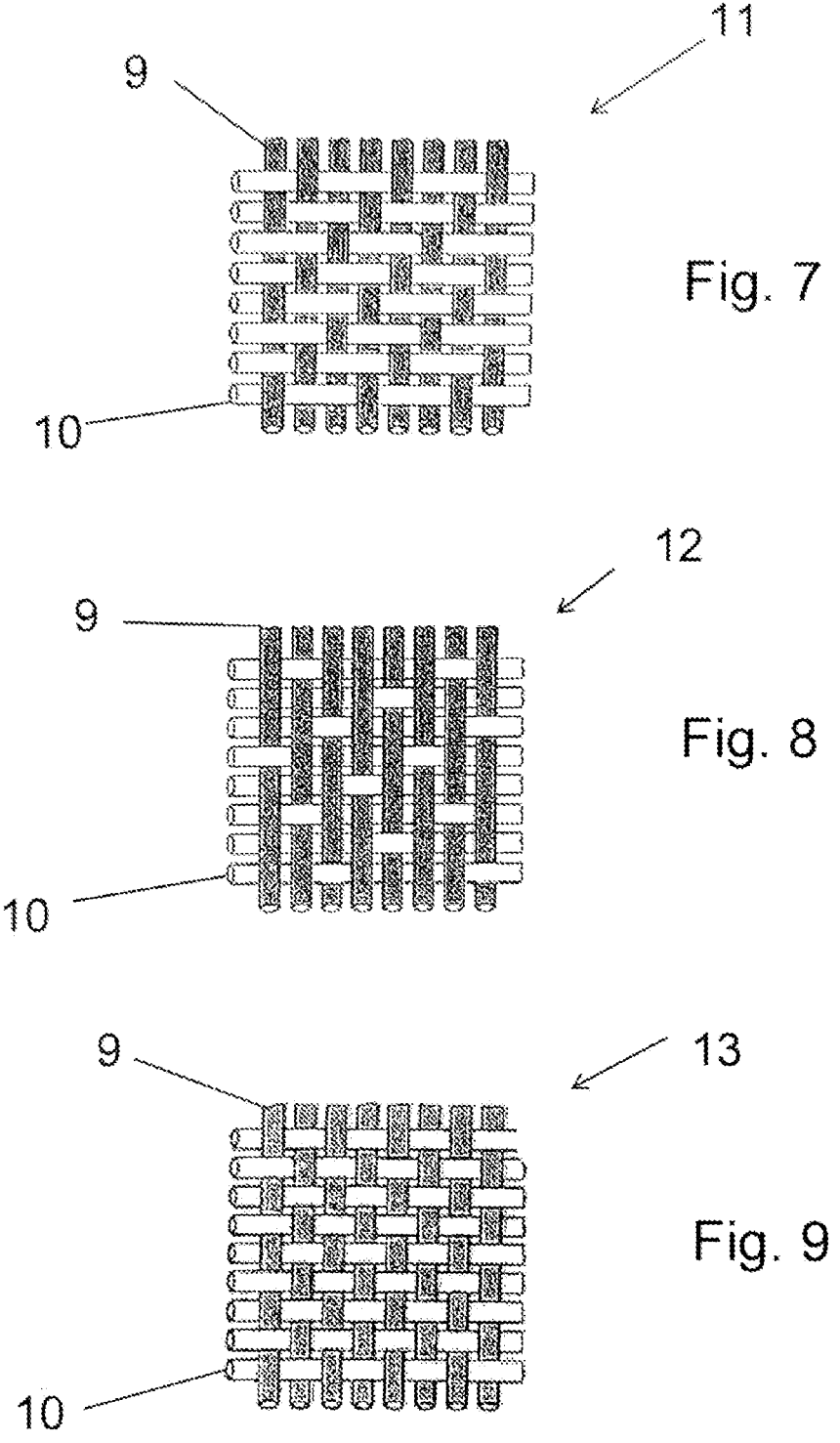
FIG. 7: shows the warp and weft threads in a twill weave.
FIG. 8: shows the warp and weft threads in a satin weave.
FIG. 9: shows the warp and weft threads in a plain weave.

In a schematic perspective view, FIG. 1 shows a first embodiment of the elastic vascular prosthesis which, as a whole, is given the designation 1. The vascular prosthesis 1 comprises a volume chamber 2 and connecting portions 3 adjacent to the volume chamber 2, for connecting the vascular prosthesis 1 to a natural cardiovascular system not shown here. The vascular prosthesis 1 is configured as a seamless, textile fabric tube consisting of warp threads 9 and weft threads 10 (FIGS. 7-9), wherein the weft threads in the region of the volume chamber 2 are formed from a highly elastic yarn 6 having a core 7 of silicone yarn, around which a yarn 8 of polyethylene terephthalate wrapping yarn is wrapped once, as shown in FIG. 6. The elastic yarn is a yarn suitable for medical purposes. The warp threads in the region of the volume chamber 2 are formed from PET multifilament yarn suitable for medical purposes. The end-side connecting portions 3 of the vascular prosthesis 1 are configured as a non-elastic woven fabric, wherein both the warp threads 9 and weft threads 10 (FIGS. 7-9) are formed from a PET multifilament yarn.

The vascular prosthesis 1 according to FIG. 1 has a dumbbell-shaped configuration, that is, in a non-pressurized state shown in FIG. 1, it is conically expanded in the region of the connecting portions 3 compared with the central region of the volume chamber 2. Here, the maximum diameter D1 in the region of the connecting portions 3 is larger by about one third than the diameter D2 in the region of the volume chamber 2, which is shown merely schematically, and not to scale, in FIG. 1.

Figure 4:
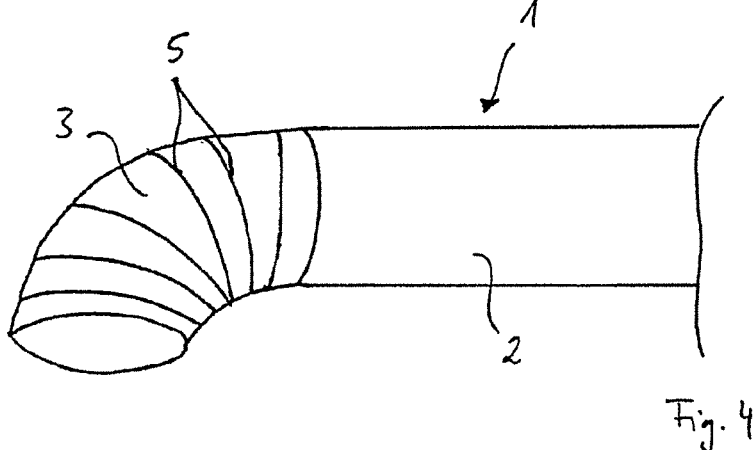
FIG. 4: shows a portion from an illustration of a fourth embodiment of the elastic vascular prosthesis.
Figure 5:
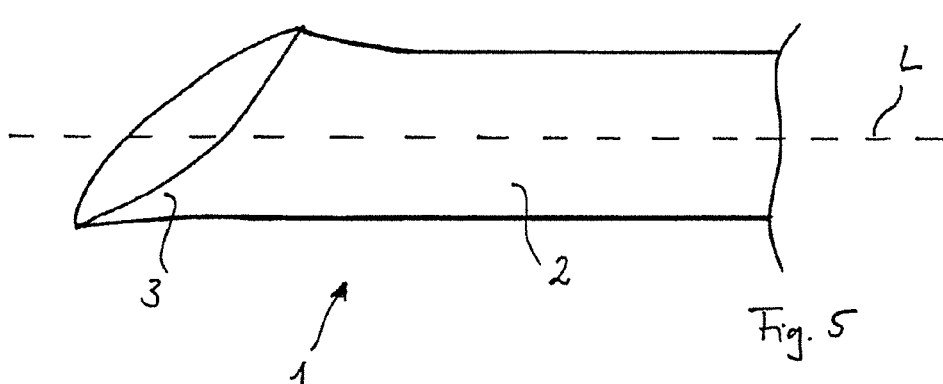
FIG. 5: shows a portion from an illustration of a fifth embodiment of the elastic vascular prosthesis.

FIG. 2 shows a second embodiment of a vascular prosthesis 1 according to the invention, wherein only one half of the symmetrically configured vascular prosthesis 1 is shown here and also in FIGS. 3 to 5. The exemplary embodiment of FIG. 2 differs from that in FIG. 1 only in that the conical expansion in the region of the connecting portions 3 is less pronounced. In the example shown here, the maximum diameter in the region of the connecting portions may be larger by maximally one fourth than the diameter in the region of the volume chamber in a non-pressurized state of the latter.

FIG. 3 shows an embodiment of the vascular prosthesis 1 having a double-layer configuration in the region of the connecting portions 3. For this purpose, the connecting portion 3 of the vascular prostheses 1 according to FIG. 3 is folded back outwards in an end portion 4, with the outer layer being sewn in a manner not shown in detail to the inner layer for the purpose of fixing it. If such a vascular prosthesis 1 is sutured to a natural blood vessel in the region of the double-layered connecting portion, a tear-out of the suture can be counteracted by the double layers.

FIG. 4 shows an embodiment of the vascular prosthesis 1 in which the diameter in the region of the connecting portions 3 substantially corresponds to the diameter in the region of the volume chamber 2 in the non-pressurized state. At the same time, the vascular prosthesis 1, in the region of the connecting portions 3, has a pleated section 5 in the circumferential direction. The pleated section 5 may be configured in a helical shape or in the form of closed rings and provides the vascular prosthesis with a high level of flexibility in the region of the connecting portions 3. In particular, the vascular prosthesis 1 can thus be prevented from kinking in the region of the connection to a natural blood vessel.

FIG. 5 shows another embodiment of the vascular prosthesis 1 according to the invention, in which end-side portions of the volume chamber 2 themselves function as connecting portions 3. In this case, the vascular prosthesis 1 as a whole is woven from a uniform elastic material, wherein the elastic yarn of silicone yarn with PET wrapping yarn is used for the weft threads, and a PET multifilament yarn is used for the warp threads. In the non-pressurized state, the vascular prosthesis 1 has a substantially uniform diameter over its entire length. The volume chamber 2 is configured in a beveled manner in the region of the connecting portions 3. The angle of the bevel is about 45° in relation to the longitudinal axis L of the vascular prosthesis 1. Thus, such a vascular prosthesis 1 is particularly suitable for being implanted as a bypass. Such a vascular prosthesis 1 can be manufactured from a corresponding textile endless tube by simply cutting it to length and providing it with a bevel in the region of the cutting edges. Beveling may in this case be carried out by means of laser cutting, for example. Particularly smooth cutting edges that do not become frayed can be realized in this manner. A vascular prosthesis configured in such a manner has a particularly simple structure and is particularly uncomplicated to produce.

Different weaving constructions may form the basis for forming the fabric tube. For example, the fabric tube may be woven with a twill weave 11 (FIG. 7) or a satin weave 12 (FIG. 8) or a plain weave 13 (FIG. 9) or with a modification of one of these weaving constructions.

The invention claimed is:

1. A replacement vascular prosthesis for connection to a natural cardiovascular system for replacement or circumvention in the form of a bypass of a portion of the aorta, the vascular prosthesis comprising a textile tube forming a volume chamber, the textile tube having opposite ends adapted to be connected in the cardiovascular system to replace or circumvent a portion of the aorta without being inserted within a vessel of the cardiovascular system, and the textile tube formed from an elastic yarn having a non-biodegradable core made from silicone yarn around which a non-biodegradable yarn made from polyethylene terephthalate (PET) is wrapped, wherein weft threads of the volume chamber are formed from the elastic yarn, and wherein warp threads of the volume chamber are formed from PET yarn, which results in the volume chamber emulating the Windkessel function of the aorta, such that the volume chamber has, in a blood pressure range below a pressure threshold value D, a pressure-expansion behavior substantially corresponding to the pressure-expansion behavior of a natural blood vessel, while the volume of the volume chamber, depending on the pressure, increases by at least 10 cm$^3$ in a blood pressure range above the pressure threshold value D.

2. The vascular prosthesis according to claim 1, wherein the silicone yarn of the core of the elastic yarn is a highly elastic silicone yarn.

3. The vascular prosthesis according to claim 1, wherein the silicone yarn is configured as a monofil made from silicone with a Shore hardness of 30 to 70.

4. The vascular prosthesis according to claim 1, wherein the elastic yarn has a thread count of 100 to 3000 dtex.

5. The vascular prosthesis according to claim 1, wherein the PET yarn forming the warp threads has a thread count of 50 to 300 dtex.

6. The vascular prosthesis according to claim 1, wherein the PET yarn forming the warp threads is configured as a multifilament yarn comprised of 20 to 300 filaments.

7. The vascular prosthesis according to claim 1, wherein the PET yarn forming the warp threads is configured as one of:

a flat yarn or textured yarn.

8. The vascular prosthesis according to claim 1, wherein the textile tube is woven in one of:

a twill weave, a satin weave or a plain weave.

9. The vascular prosthesis according to claim 1, wherein the vascular prosthesis comprises connecting portions adjacent to the volume chamber, for connection to the natural cardiovascular system, wherein the connecting portions have a lower elasticity than the volume chamber.

10. The vascular prosthesis according to claim 1, wherein end-side portions of the volume chamber function as connecting portions for connection to the natural cardiovascular system, wherein the vascular prosthesis has a uniform elasticity in the region of the volume chamber inclusive of the connecting portions.

11. The vascular prosthesis according to claim 9, wherein the vascular prosthesis has a double-layer configuration in the region of the connecting portions.

12. The vascular prosthesis according to claim 9, wherein the vascular prosthesis has a dumbbell-shaped configuration such that, in a non-pressurized state, it is conically expanded in the region of the connecting portions compared with a central region of the volume chamber.

13. The vascular prosthesis according to claim 1, wherein the silicone yarn is configured as a monofil made from silicone with a Shore hardness of 40 to 60.

14. The vascular prosthesis according to claim 1, wherein the elastic yarn has a thread count of 200 to 2000 dtex.

15. The vascular prosthesis according to claim 1, wherein the volume of the volume chamber remains substantially unchanged below a pressure threshold value D of 100 mmHg, and does not change beyond minimum expansions required for maintaining the Windkessel function.

16. The vascular prosthesis according to claim 1, wherein upon reaching the pressure threshold value D, the volume of the volume chamber increases by 10 to 80 cm$^3$.

* * * * *